(12) United States Patent
Yamada et al.

(10) Patent No.: US 7,816,582 B2
(45) Date of Patent: Oct. 19, 2010

(54) ARABINOGALACTAN PROTEIN HAVING ACTIVITY OF IMPROVING TOLERANCE TO HEAT OR MOISTURE STRESS

(75) Inventors: Akiyo Yamada, Fuchu (JP); Yoshihiro Ozeki, Fuchu (JP); Satoko Akatsuka, Tokyo (JP)

(73) Assignee: National University Corporation Tokyo University of Agriculture and Technology, Tokyo (JP)

( * ) Notice: Subject to any disclaimer, the term of this patent is extended or adjusted under 35 U.S.C. 154(b) by 713 days.

(21) Appl. No.: 11/573,010

(22) PCT Filed: Aug. 1, 2005

(86) PCT No.: PCT/JP2005/014014

§ 371 (c)(1),
(2), (4) Date: Apr. 6, 2007

(87) PCT Pub. No.: WO2006/013807

PCT Pub. Date: Feb. 9, 2006

(65) Prior Publication Data

US 2008/0307548 A1  Dec. 11, 2008

(30) Foreign Application Priority Data

Aug. 6, 2004  (JP)  ............... 2004-231603

(51) Int. Cl.
*A01H 1/00* (2006.01)
*C07H 21/04* (2006.01)
*C12N 15/00* (2006.01)
*C12N 15/29* (2006.01)

(52) U.S. Cl. ................. 800/295; 435/6; 435/468; 435/419; 435/252.3; 435/320.1; 530/370; 536/23.6; 800/278; 800/289

(58) Field of Classification Search ............. 435/6, 435/69.1, 468, 419, 320.1; 536/23.6; 800/278, 800/295, 289; 530/370
See application file for complete search history.

(56) References Cited

U.S. PATENT DOCUMENTS

2004/0031072 A1* 2/2004 La Rosa et al. ............ 800/278

FOREIGN PATENT DOCUMENTS

WO  WO 02/079245 A2  10/2002

OTHER PUBLICATIONS

Satoko Akatsuka et al., "Expression of Salicornia europaea Arabinogalactan Protein Enhances Slat Tolerance in *Escherichia coli*," Plant Cell Physiol., vol. 46, Supplement, Mar. 2005, p. S161.
UniProt Consortium, Database Accession No. Q8H3S1, "Putative fasciclin-like arabinogalactan-protein," UniProtKB/TrEMBL Database, XP 002457595, Mar. 1, 2003, pp. 1-2.
Schultz et al., "Using Genomic Resources to Guide Research Directions. The Arabinogalactan Protein Gene Family as a Test Case" Plant Physiol., Aug. 2002, vol. 129, pp. 1448-1463.
Yamada et al., "Expression of Mangrove Allene Oxide Cyclase Enhances Salt Tolerance in *Escherichia coli*, Yeast and Tobacco Cells", Plant Cell Physiol., 2002, vol. 43, No. 8, pp. 903-910.
Akatsuka et al., "Establishment of Culture Cells System of Saltwort Salicornia Europaea", Dai 45 Kai The Japanese Society of Plant Physiologists Nenkai Yoshi, Mar. 2004, p. 195, 2aI12(378) (in Japanese with translation).

* cited by examiner

*Primary Examiner*—Phuong T Bui
(74) *Attorney, Agent, or Firm*—Kenneth H. Sonnenfeld; King & Spalding LLP (57) ABSTRACT

It is intended to provide a gene encoding a protein having an activity of improving a tolerance to an environmental stress such as salt, moisture, or heat stress, in particular, a tolerance to water stress; a protein having an activity of improving a tolerance to an environmental stress; a transgenic plant having an enhanced tolerance to an environmental stress, and so on. A halophyte *Salicornia europaea*, which has a strong activity of improving a tolerance to water stress and can grow even in a dry area with much salt accumulation, was used to search genes participating in the salt tolerance of *Salicornia europaea* by a functional screening method using an *Escherichia coli* gene expression system, with the aim of isolating genes (cDNAs) participating in the salt-tolerance mechanism of *Salicornia europaea*. As a result, it was found out that an arabinogalactan protein consisting of 427 amino acids and having partial homology to a Fasciclin-like arabinogalactan protein of *Arabidopsis thaliana* has a function of enhancing salt tolerance, water stress tolerance (sorbitol tolerance), and heat tolerance.

10 Claims, 5 Drawing Sheets

Figure 1

```
TCGCTACTTAGCTCCCACTCTTTCTACTAAATATTATTTCCACTTCTCATTCCCACTCAT
TTTTTCCTCTAACTTCCACTCTTAACACAACTGTCTAGTGTCTACTAACCCAACCAAC
CATGCAAAAAGCTATAGTATTAGGAGGATTGCTCCTCTTGCTGACACTCACCCTCACC
CCCACCACAACACATGCCCACAACATCACCAAAATTCTAGCCAAGTTCCCTGATTTC
TCCTCCTTCAACCACTACCTCACCACCACCCACCTCGCCCCTGAGATCAACACCCGC
CAAACCATCACCGTCCTCGCCATCGACAATGCCGCCATGGCTTCCCTCACCTCCAAG
CACCTCCGCATTTCCACCCTCAAAAAGATCCTCTCCCTCCAGGTCCTCCTCGATTACT
TCGGCGCTAAAAAACTCCACCAAATCACCGACGGCTCTGCCCTTGCTGCCACCATGT
ACCAAGCCACCGGCTCCGCCCCCGGCACTGCCGGTTTTGTCAACATCACCGACCTCA
AAGGCGGCAAAGTCGGCTTCGCCGCCACCAACCCCGCCTCTGATGAAGGCGATTCC
GACAGCACACCCTCTCTCAACTCAAGCTTCATCAAATCCCTAAAGGAAATCCCTTAC
AACATCTCAGTCATCCAAATCAGCCACATTCTATCCTCACCTACCGCCGAGGCGCCTT
CTCCGGCGCCCGAAGCCACCAACATCACCGGCATTATGTCCGCTCACGGCTGCAAGG
AATTCGCCGACACGCTGACGTCATTTCCCGACGCACTCGAGGTTTTCACCACCAACA
CAGAAGGCGGATTAACCGTCTTTTGTCCTTCAGACGACGCCTTCAAAGGCTTCGTCC
CTAATTTCAAAAACCTAACAAAAGAAGAAAAAAACTCTCTGCTACTCTTCCATGGAA
TTCCTGTCTACAACTCCATGGCATTGCTCAAAACCAGCAATGGAGTGATGAACACTC
TCGCTACCGACGGTAAGAACAAATTCGACTTCACTGTTCAAAACGCAGGTCAGAAA
GTGACATTGAAGACGAAGGCTGTCACCGCGACCATCACCGCTACTCTGTTGGACGA
AGATCCACTTGCCGATCTACACCATTGATAAGGTCTTGAAGCCATCGGAGATGTTTAAG
AAGCCGCAGATTTCACCTGCACCAGCACCTGCTCCGGAAGCTGAGGCGCCTTCGAA
GGGTAAAAGACACCATAAATCGCCAGCAGCGCCACCGAGTGAAGATGATTCGGCGG
ATTCTCCGGCGGACTCACCGGCAGATGGACCGAATGCGGATGACTCGACGGCGGAC
GATTCGAGCGACGGAGGAGAGAGAGTGAAGAAAGGGTTTTGGATGGTTGGAGTTGT
GTCGGTGGTAGGGGTTTGGAGTATGTGGATATAGAATTACACAAAAAAAAAAAAAA
GGGTAATGAAATATGAAAAGGGAATAATTTAATTTAATTTGGGGGGTAAGAAAATGG
AAGTGTAATTTATATTTATGGTGTGCCCAAATTATTATTGTCCTGTAATTTTATTTTTTCT
TTTTAATTTTTTTAGTTAGGATTTTGTGTGAGAATTGTTTGTTTGTTGTGTTTGAGTG
TTGTTTAATGTAATTTTTTGAATGGGATTAGGATTTTATGTGGGTGTTTAAAAGAAAAA
TAATTGGATTGAAATTTGTTTTTGGTATCACAAATTGTAGACACACATAAATTTGACAAT
AATTTATGGTGATGTATCAATTAATCTGAAAAAAAAAAAAAAAA
```

Figure 2

MQKAIVLGALLLELLTLTLTPTTTHAHNITKILAKFPDFSSFNHYLTTTHLAPEINTRQTITV
LAIDNAAMASLTSKHLPISTLKNILSLHVLLDYFGAKKLHQITDGSALAATMYQATGSAP
GTAGFVNITDLKGGKVGFAATNPASDEGDSDSTPSLNSTRIKSLKEIPYNISVIQISHILSSP
TAEAPSPAPEATNITGIMSAHGCKEFADTBTSFPDALEVFTINTEGGLTVFGPSDDAFKGF
LPNFKNLTKEEKNSLLLFHGIPVYNSMALLKTSNGVMNTLATDGKNKFDFTVQNAGQK
VTLKTKAVTATITATLLDEDPVAIYTIDKVLKPSEIPKKPEISPAPAPAPEAEAPSKGKRHH
KSPPAPPSEDDSADSPADSPADGPNADDSTADDSSDGGERVKKGFWMVGVVSVVGVW
SMWI

Figure 3

Secretory signal-like sequence
Fasciclin-like sequence
GPI anchor signal-like sequence
Non-coding region

SEQUENCE LISTING

```
<160> NUMBER OF SEQ ID NOS: 6

<210> SEQ ID NO 1
<211> LENGTH: 1765
<212> TYPE: DNA
<213> ORGANISM: Salicornia europaea

<400> SEQUENCE: 1
tcgctactta gctcccactc tttctactaa atattatttc cacttctcat tcccactcat     60
tttttcctct aacttccact cttaacacaa ctgtctagtg tctactaacc caaccaacca    120
tgcaaaaagc tatagtatta ggagcattgc tcctcttgct cacactcacc ctcaccccca    180
ccacaacaca tgcccacaac atcaccaaaa ttctagccaa gttccctgat ttctcctcct    240
tcaaccacta cctcaccacc acccacctcg ccctgagat caacacccgc caaaccatca    300
ccgtcctcgc catcgacaat gccgccatgg cttccctcac ctccaagcac ctccccattt    360
ccaccctcaa aaacatcctc tccctccacg tcctcctcga ttacttcggc gctaaaaaac    420
tccaccaaat caccgacggc tctgcccttg ctgccaccat gtaccaagcc accggctccg    480
cccccggcac tgccggtttt gtcaacatca ccgacctcaa aggcggcaaa gtcggcttcg    540
ccgccaccaa ccccgcctct gatgaaggcg attccgacag cacaccctct ctcaactcaa    600
ccttcatcaa atccctaaag gaaatccctt acaacatctc agtcatccaa atcagccaca    660
ttctatcctc acctaccgcc gaggcgcctt ctccggcgcc cgaagccacc aacatcaccg    720
gcattatgtc cgctcacggc tgcaaggaat tgccgacac gctgacgtca tttcccgacg    780
cactcgaggt tttcaccacc aacacagaag gcggattaac cgtcttttgt ccttcagacg    840
acgccttcaa aggcttcctc cctaatttca aaaacctaac aaaagaagaa aaaaactctc    900
tgctactctt ccatggaatt cctgtctaca actccatggc attgctcaaa accagcaatg    960
gagtgatgaa cactctcgct accgacggta agaacaaatt cgacttcact gttcaaaacg   1020
caggtcagaa agtgacattg aagacgaagg ctgtcaccgc gaccatcacc gctactctgt   1080
tggacgaaga tccagttgcg atctacacca ttgataaggt cttgaagcca tcggagatct   1140
ttaagaagcc ggagatttca cctgcaccag cacctgctcc ggaagctgag gcgccttcga   1200
agggtaaaag acaccataaa tcgccaccag cgccaccgag tgaagatgat tcggcggatt   1260
```

```
ctccggcgga ctcaccggca gatggaccga atgcggatga ctcgacggcg gacgattcga    1320
gcgacggagg agagagagtg aagaaagggt tttggatggt tggagttgtg tcggtggtag    1380
gggtttggag tatgtggata tagaattaca caaaaaaaaa aaaaagggta atgaaatatg    1440
aaaagggaat aatttaattt aatttggggg gtaagaaaat ggaagtgtaa tttatattta    1500
tggtgtgccc aaattattat tgtcctgtaa ttttattttt tcttttaat ttttttagtt     1560 aggattttgt gtgagaattt gtttgtttgt tgtgtttgag tgttgtttaa tgtaattttt    1620
tgaatgggat taggatttta tgtgggtgtt taaagaaaa ataattggat tgaaatttgt     1680
ttttggtatc acaaattgta gacacacata atttgacaat aatttatggt gatgtatcaa    1740
ttaatctgaa aaaaaaaaaa aaaaa                                          1765

<210> SEQ ID NO 2
<211> LENGTH: 427
<212> TYPE: PRT
<213> ORGANISM: Salicornia europaea

<400> SEQUENCE: 2

Met Gln Lys Ala Ile Val Leu Gly Ala Leu Leu Leu Leu Thr Leu
1               5                   10                  15

Thr Leu Thr Pro Thr Thr Thr His Ala His Asn Ile Thr Lys Ile Leu
            20                  25                  30

Ala Lys Phe Pro Asp Phe Ser Ser Phe Asn His Tyr Leu Thr Thr Thr
        35                  40                  45

His Leu Ala Pro Glu Ile Asn Thr Arg Gln Thr Ile Thr Val Leu Ala
    50                  55                  60

Ile Asp Asn Ala Ala Met Ala Ser Leu Thr Ser Lys His Leu Pro Ile
65                  70                  75                  80

Ser Thr Leu Lys Asn Ile Leu Ser Leu His Val Leu Leu Asp Tyr Phe
                85                  90                  95

Gly Ala Lys Lys Leu His Gln Ile Thr Asp Gly Ser Ala Leu Ala Ala
            100                 105                 110

Thr Met Tyr Gln Ala Thr Gly Ser Ala Pro Gly Thr Ala Gly Phe Val
        115                 120                 125

Asn Ile Thr Asp Leu Lys Gly Gly Lys Val Gly Phe Ala Ala Thr Asn
    130                 135                 140

Pro Ala Ser Asp Glu Gly Asp Ser Asp Ser Thr Pro Ser Leu Asn Ser
145                 150                 155                 160

Thr Phe Ile Lys Ser Leu Lys Glu Ile Pro Tyr Asn Ile Ser Val Ile
                165                 170                 175

Gln Ile Ser His Ile Leu Ser Ser Pro Thr Ala Glu Ala Pro Ser Pro
            180                 185                 190

Ala Pro Glu Ala Thr Asn Ile Thr Gly Ile Met Ser Ala His Gly Cys
        195                 200                 205

Lys Glu Phe Ala Asp Thr Leu Thr Ser Phe Pro Asp Ala Leu Glu Val
        210                 215                 220

Phe Thr Thr Asn Thr Glu Gly Gly Leu Thr Val Phe Cys Pro Ser Asp
225                 230                 235                 240

Asp Ala Phe Lys Gly Phe Leu Pro Asn Phe Lys Asn Leu Thr Lys Glu
                245                 250                 255

Glu Lys Asn Ser Leu Leu Leu Phe His Gly Ile Pro Val Tyr Asn Ser
            260                 265                 270

Met Ala Leu Leu Lys Thr Ser Asn Gly Val Met Asn Thr Leu Ala Thr
        275                 280                 285
```

```
Asp Gly Lys Asn Lys Phe Asp Phe Thr Val Gln Asn Ala Gly Gln Lys
    290                 295                 300

Val Thr Leu Lys Thr Lys Ala Val Thr Ala Thr Ile Thr Ala Thr Leu
305                 310                 315                 320

Leu Asp Glu Asp Pro Val Ala Ile Tyr Thr Ile Asp Lys Val Leu Lys
                325                 330                 335

Pro Ser Glu Ile Phe Lys Lys Pro Glu Ile Ser Pro Ala Pro Ala Pro
            340                 345                 350

Ala Pro Glu Ala Glu Ala Pro Ser Lys Gly Lys Arg His His Lys Ser
        355                 360                 365

Pro Pro Ala Pro Pro Ser Glu Asp Asp Ser Ala Asp Ser Pro Ala Asp
    370                 375                 380

Ser Pro Ala Asp Gly Pro Asn Ala Asp Asp Ser Thr Ala Asp Asp Ser
385                 390                 395                 400

Ser Asp Gly Gly Glu Arg Val Lys Lys Gly Phe Trp Met Val Gly Val
                405                 410                 415

Val Ser Val Val Gly Val Trp Ser Met Trp Ile
            420                 425

<210> SEQ ID NO 3
<211> LENGTH: 30
<212> TYPE: DNA
<213> ORGANISM: Artificial Sequence
<220> FEATURE:
<223> OTHER INFORMATION: F1 primer

<400> SEQUENCE: 3
cccaccacaa cataaatgca caacatcacc                                    30

<210> SEQ ID NO 4
<211> LENGTH: 22
<212> TYPE: DNA
<213> ORGANISM: Artificial Sequence
<220> FEATURE:
<223> OTHER INFORMATION: T7 primer

<400> SEQUENCE: 4
gtaatacgac tcactatagg gc                                            22

<210> SEQ ID NO 5
<211> LENGTH: 30
<212> TYPE: DNA
<213> ORGANISM: Artificial Sequence
<220> FEATURE:
<223> OTHER INFORMATION: F2 primer

<400> SEQUENCE: 5
gtctagtgtc tactaaccca accaaccatg                                    30

<210> SEQ ID NO 6
<211> LENGTH: 30
<212> TYPE: DNA
<213> ORGANISM: Artificial Sequence
<220> FEATURE:
<223> OTHER INFORMATION: R1 primer

<400> SEQUENCE: 6
ctctcctccg tctcactaat cgtccgccgt                                    30
```

ARABINOGALACTAN PROTEIN HAVING ACTIVITY OF IMPROVING TOLERANCE TO HEAT OR MOISTURE STRESS

TECHNICAL FIELD

The present invention relates to a DNA encoding an arabinogalactan protein having an activity of improving a tolerance to at least heat or water stress, an arabinogalactan protein having an activity of improving a tolerance to at least heat or water stress, and use of the DNA or the protein of a transgenic plant and so on.

BACKGROUND ART

Organisms existing in the natural world are exposed to a variety of environmental stresses such as salt, high temperature, low temperature, freezing, drying, and water stresses. Particularly, the salt stress is one of the biggest factors that inhibit the growth of many higher plants. Since the enhanced salt tolerance of higher plants leads to increase in the production of agricultural products, attempts to enhance the salt tolerance of higher plants by gene transfer have been made actively. Proteins having a function of enhancing salt tolerance can be divided broadly into compatible solute (glycine-betaine, mannitol, trehalose, or proline)-synthesizing enzymes, enzymes ($Na^+/H^+$ antiporters) participating in ion homeostasis and transcriptional regulators that regulate the expression of their genes. Many cases have been reported in recent years in which improvement in salt tolerance has been observed in transformed cells with the expression of these proteins. For example, there have been reported a plant of the genus Eucalyptus comprising a choline oxidase-encoding gene introduced in the chromosomal DNA (see Patent Document 1), a DNA encoding an $Na^+/H^+$ antiporter derived from a salt tolerance blue-green alga (*Aphanothece halophytica*) (see Patent Document 2), and a method for increasing a stress tolerance of a plant, characterized by suppressing the expression of a gene encoding an enzyme of the intracellular proline degradation system of the plant (see Patent Document 3). However, transformants that tolerate sea water containing approximately 500 mM NaCl have not been obtained yet for organisms (particularly, plants) with the expression of these factors enhancing salt tolerance. Only the compatible solute synthesis-system enzymes or enzymes participating in ion homeostasis seem to be insufficient for constructing transformants that tolerate sea water.

On the other hand, plants (halophytes), which have acquired a strong salt-tolerance mechanism during their evolutional processes, are present in the natural world. It has been expected that transformants (particularly, plants) that have acquired strong salt tolerance comparable to that of halophytes can be produced by using the salt tolerance factors of such plants alone or in combination of several of them. For example, the present inventors paid attention to mangrove, one of halophytes. The present inventors obtained cultured cells separated from the already-established cultured cell line of *Bruguiera sexangula*, and successfully enhanced the salt tolerance of yeast, a plant cell (cultured tobacco cell), and a plant (tobacco) by culturing this cell line in the presence of 100 mM NaCl, preparing a cDNA library on the basis of mRNA extracted from the cultured cells, attempting to search genes participating in the salt tolerance of mangrove from the library, and introducing one gene among the isolated genes participating in stress tolerance (see Patent Document 4). Moreover, the present inventors found a novel salt tolerance-increasing gene in *Kandelia candel* (L.) Druce, which is one species of mangrove, and determined the nucleotide sequence of the gene and amino acids encoded thereby. It has further been confirmed that the introduction of the gene into a different plant increases the salt tolerance of the different plant (see Patent Documents 5 and 6). However, findings on a salt tolerance factor derived from a halophyte are very few until now.

Patent Document 1: Japanese Laid-Open Patent Application No. 2003-143988

Patent Document 2: Japanese Laid-Open Patent Application No. 2003-180373

Patent Document 3: Japanese Laid-Open Patent Application No. 2003-186879

Patent Document 4: Japanese Laid-Open Patent Application No. 2001-333784

Patent Document 5: Japanese Laid-Open Patent Application No. 2003-116546

Patent Document 6: Published Japanese translation of PCT international publication No. 2003-512837

DISCLOSURE OF THE INVENTION

Object to be Solved by the Present Invention

An object of the present invention is to provide a gene encoding a protein having an activity of improving a tolerance to an environmental stress such as salt, moisture, or heat stress, in particular, a tolerance to heat or water stress; a protein having an activity of improving a tolerance to an environmental stress; and a transgenic plant having an enhanced tolerance to an environmental stress, and so on.

Means to Solve the Object

The present inventors paid attention to *Salicornia europaea*, one of halophytes having the strongest salt tolerance, which is an annual herb belonging to the family Chenopodiaceae and forming community in a salt marsh and can grow even in an environment containing approximately 1 M NaCl. *Salicornia europaea* can be said to be a valuable genetic resource for enhancing the salt tolerance of higher plants. However, findings on the salt tolerance gene of *Salicornia europaea* have hardly been obtained so far. The main reason thereof may be that this species is on a downward trend (listed as an endangered species) due to the development of the coast, and the plant material is difficult to be stably obtained in proceeding with research. Therefore, the present inventors pursued the establishment of a cultured cell line capable of stably growing in laboratories. As a result, three types of callus lines, that is, red, green, and white calluses, could be maintained stably by continuing culture under light and dark conditions. Evaluation results of the growth of these three lines of calluses in the presence of salt demonstrated that all the lines can grow in the presence of an exceedingly high concentration of salt containing 400 mM NaCl.

Next, to analyze in detail the salt-tolerance mechanism of *Salicornia europaea* at a cellular level, the establishment of a suspension-cultured cell line was attempted. As a result, only the white-line calluses were successfully converted into suspension-cultured cells. When this suspension-cultured cell was used to evaluate salt tolerance, the fresh weight was 135 mg/ml in approximately 3 weeks after initiation of culture in a liquid medium free from NaCl, whereas the fresh weight reached 195 mg/ml in a medium containing 100 mM NaCl. Moreover, the fresh weight was 124 mg/ml in a medium containing 300 mM NaCl, indicating growth almost equal to that under the condition of 0 mM NaCl. In the general establishment of cultured cell lines from halophytes, the obtained cultured cells often lose salt tolerance. However, the obtained suspension-cultured cell of Salicornia europaea maintained strong salt tolerance that reflects the salt tolerance (halophilism) shown by the plant. When a sodium ion content in the suspension-cultured cell of Salicornia europaea was chronologically measured by use of ion chromatography, a tendency to intracellularly accumulate sodium ions was observed in culture in both media containing 100 mM NaCl, and 300 mM NaCl, respectively. This seemed to be because a tendency similar to the phenomenon in which Salicornia europaea accumulates a high concentration of salt in its leaf was exhibited. From these results, the obtained suspension-cultured cell of Salicornia europaea could be expected to serve as a good model system for analyzing the strong salt-tolerance mechanism of Salicornia europaea at a cellular level. Thus, genes participating in the salt tolerance of Salicornia europaea was searched by a functional screening method using an Escherichia coli gene expression system, with the aim of isolating genes (cDNAs) participating in the salt-tolerance mechanism of Salicornia europaea. As a result, the present inventors have completed the present invention by finding out that an arabinogalactan protein consisting of 427 amino acids and having partial homology to a Fasciclin-like arabinogalactan protein of Arabidopsis thaliana has a function of enhancing salt tolerance, water stress tolerance (sorbitol tolerance), and heat tolerance. It has not been known yet that the arabinogalactan protein has an activity of improving a tolerance to heat or water stress. This activity of enhancing water stress tolerance (sorbitol tolerance) and heat tolerance possessed by the arabinogalactan protein is considered to require the amino acid sequence (1 to 25) of a putative secretory signal peptide or the amino acid sequence (401 to 427) of a putative GPI anchor signal sequence. A case in which the water stress or heat stress tolerance of a microorganism is improved by a secretory protein has not been known so far.

Specifically, the present invention relates to (1) a DNA encoding a protein consisting of the amino acid sequence represented by SEQ ID NO: 2; (2) a DNA encoding a protein consisting of an amino acid sequence having 70% or higher homology to the amino acid sequence represented by SEQ ID NO: 2 and having an activity of improving a tolerance to at least heat or water stress; (3) a DNA encoding a protein consisting of an amino acid sequence wherein one or a few amino acids are deleted, substituted, or added in the amino acid sequence represented by SEQ ID NO: 2 and having an activity of improving a tolerance to at least heat or water stress; (4) a DNA consisting of the nucleotide sequence represented by SEQ ID NO: 1 or a complementary sequence thereof; (5) a DNA consisting of a nucleotide sequence wherein one or a few amino bases are deleted, substituted, or added in the nucleotide sequence represented by SEQ ID NO: 1 and encoding a protein having an activity of improving a tolerance to at least heat or water stress; and (6) a DNA hybridizing under stringent conditions to the DNA according to (4) or (5) and encoding a protein having an activity of improving a tolerance to at least heat or water stress.

The present invention also relates to (7) a protein consisting of the amino acid sequence represented by SEQ ID NO: 2; (8) a protein consisting of an amino acid sequence having 70% or higher homology to the amino acid sequence represented by SEQ ID NO: 2 and having an activity of improving a tolerance to at least heat or water stress; (9) a protein consisting of an amino acid sequence wherein one or a few amino acids are deleted, substituted, or added in the amino acid sequence represented by SEQ ID NO: 2 and having an activity of improving a tolerance to at least heat or water stress; (10) a recombinant vector comprising a DNA encoding the protein according to any one of (7) to (9); (11) a recombinant vector comprising the DNA according to any one of (1) to (6); and (12) a transformed cell obtained by introducing the recombinant vector according to (10) or (11) into a host cell.

The present invention further relates to (13) the transformed cell according to (12), wherein the host cell is a plant cell; (14) the transformed cell according to (12), wherein the host cell is a microorganism cell; (15) a method for producing a protein having an activity of improving a tolerance to at least heat or water stress, comprising culturing the transformed cell according to any one of (12) to (14), and recovering a recombinant protein from the transformed cell or a supernatant of the culture solution thereof; (16) a transgenic plant having an activity of improving a tolerance to at least heat or water stress, which is obtained by introducing a DNA encoding the protein according to any one of (7) to (9) into a plant cell and allowing the plant cell to divide, proliferate, and redifferentiate; (17) a transgenic plant having an activity of improving a tolerance to at least heat or water stress, which is obtained by introducing the DNA according to any one of (1) to (6) into a plant cell and allowing the plant cell to divide, proliferate, and redifferentiate; and (18) a transgenic plant having an activity of improving a tolerance to at least heat or water stress, which is obtained by introducing the vector according to (12) or (13) into a plant cell and allowing the plant cell to divide, proliferate, and redifferentiate.

EFFECT OF THE INVENTION

The DNA encoding a protein having an activity of improving a tolerance to at least heat or water stress of the present invention is a gene derived from a halophyte and as such, can be expected to be utilized in the improvement of the tolerance of a wide range of organisms such as higher plants and microorganisms to an environmental stress (salt, moisture, heat stress, etc). Particularly, cultivable lands have been decreasing drastically in recent years due to salt accumulation in soil. Thus, the present invention can be used in the productivity improvement of agriculture and the greening of deserts. In the production of useful substances such as amino acids using microorganisms, the phenomenon is known in which water stress caused by the products (metabolites) adversely affects the abilities of the microorganisms to produce useful substances. However, according to the present invention, useful substances can be produced without undergoing the adverse effect of water stress. Furthermore, the achievements obtained by the present invention can also be applied to various microorganism industries.

BEST MODE OF CARRYING OUT THE INVENTION

The DNA of the present invention is not particularly limited as long as it is (A) a DNA encoding a protein consisting of the amino acid sequence represented by SEQ ID NO: 2; (B) a DNA encoding a protein consisting of an amino acid sequence having 70% or higher homology to the amino acid sequence represented by SEQ ID NO: 2 and having an activity of improving a tolerance to at least heat or water stress; (C) a DNA encoding a protein consisting of an amino acid sequence wherein one or a few amino acids are deleted, substituted, or added in the amino acid sequence represented by SEQ ID NO: 2 and having an activity of improving a tolerance to at least heat or water stress; (D) a DNA consisting of the nucleotide sequence represented by SEQ ID NO: 1 or a complementary sequence thereof; (E) a DNA consisting of a nucleotide sequence wherein one or a few bases are deleted, substituted, or added in the nucleotide sequence represented by SEQ ID NO: 1 and encoding a protein having an activity of improving a tolerance to at least heat or water stress; or (F) a DNA hybridizing under stringent conditions to the DNA (D) or (E) and encoding a protein having an activity of improving a tolerance to at least heat or water stress. The protein of the present invention is not particularly limited as long as it is (A) a protein consisting of the amino acid sequence represented by SEQ ID NO: 2; (B) a protein consisting of an amino acid sequence having 70% or higher homology to the amino acid sequence represented by SEQ ID NO: 2 and having an activity of improving a tolerance to at least heat or water stress; or (C) a protein consisting an amino acid sequence wherein one or a few amino acids are deleted, substituted, or added in the amino acid sequence represented by SEQ ID NO: 2 and having an activity of improving a tolerance to at least heat or water stress. In this context, an "activity of improving a tolerance to water stress" refers to an activity showing an improved tolerance to a predetermined concentration of sorbitol. For example, a plant or microorganism expressing a protein having the activity of improving a tolerance to water stress shows statistically significantly excellent proliferation in the presence of a predetermined concentration of sorbitol, as compared with a plant or microorganism not expressing the protein. However, the "activity of improving a tolerance to water stress" is not limited to this example. Moreover, the "activity of improving a tolerance to heat stress" refers to an activity showing an improved tolerance to high temperatures. For example, a plant or microorganism expressing a protein having the activity of improving a tolerance to heat stress shows statistically significantly excellent proliferation at high temperatures, as compared with a plant or microorganism not expressing the protein. However, the "activity of improving a tolerance to heat stress" is not limited to this example.

The DNA of the present invention encodes a protein having an activity of improving a tolerance to at least heat or water stress and, preferably, further encodes a protein having an activity of improving a tolerance to an environmental stress such as salt, in addition to the activity of improving a tolerance to heat stress or the activity of improving a tolerance to water stress. The protein of the present invention has an activity of improving a tolerance to at least heat or water stress and, preferably, further has an activity of improving a tolerance to an environmental stress such as salt, in addition to the activity of improving a tolerance to heat stress or the activity of improving a tolerance to water stress.

The above-mentioned "amino acid sequence wherein one or a few amino acids are deleted, substituted, or added" means an amino acid sequence wherein any number of amino acids, for example, 1 to 30, preferably 1 to 15, more preferably 1 to 10, even more preferably 1 to 5 amino acids are deleted, substituted or added. The above-mentioned "nucleotide sequence wherein one or a few bases are deleted, substituted, or added" means a nucleotide sequence wherein any number of bases, for example, 1 to 20, preferably 1 to 15, more preferably 1 to 10, even more preferably 1 to 5 bases are deleted, substituted, or added. The amino acid sequence wherein a few amino acids are deleted can be exemplified specifically by an amino acid sequence having deletion of N-terminal 25 amino acid residues or an amino acid sequence having deletion of C-terminal 8 amino acid residues.

For example, a DNA consisting of a nucleotide sequence wherein one or a few bases are deleted, substituted, or added (mutant DNA) can also be prepared by any method known by those skilled in the art such as chemical synthesis, a genetic engineering approach, or mutagenesis. Specifically, the mutant DNA can be obtained by introducing a mutation into the DNA consisting of the nucleotide sequence represented by SEQ ID NO: 1 through the use of a method wherein this DNA is subjected to contact and act with a drug serving as a mutagen, a method wherein this DNA is irradiated with ultraviolet rays, a genetic engineering approach, or the like. A site-specific mutagenesis method, one of genetic engineering approaches, is useful because it is an approach that can introduce a particular mutation at a particular position. The site-specific mutagenesis can be performed in accordance with a method described in, for example, Molecular Cloning: A laboratory Manual, 2nd Ed., Cold Spring Harbor Laboratory, Cold Spring Harbor, N.Y., 1989 (hereinafter, abbreviated to "Molecular Cloning 2nd Ed.") or Current Protocols in Molecular Biology, Supplement 1 to 38, John Wiley & Sons (1987-1997). By expressing this mutant DNA with an appropriate expression system, a protein consisting of the amino acid sequence wherein one or a few amino acids are deleted, substituted, or added can be obtained.

The above-mentioned "amino acid sequence having at least 70% or higher homology to the amino acid sequence represented by SEQ ID NO: 2" is not particularly limited as long as its homology to the amino acid sequence represented by SEQ ID NO: 2 is 70% or higher, and refers to a homology of, for example, 70% or higher, preferably 80% or higher, more preferably 90% or higher, even more preferably 95% or higher, particularly preferably 98% or higher, most preferably 99% or higher homology.

The above-mentioned "DNA hybridizing under stringent conditions" means a DNA obtained by using a nucleic acid such as DNA or RNA as a probe and performing, for example, a colony hybridization, plaque hybridization, or southern blot hybridization method. Specific examples thereof can include DNA that can be identified by using a filter comprising colony- or plaque-derived DNA or a fragment of the DNA immobilized thereon to perform hybridization at 65° C. in the presence of 0.7 to 1.0 M NaCl and then using approximately 0.1-fold to 2-fold SSC solution (the composition of a 1-fold concentration of SSC solution is 150 mM sodium chloride and 15 mM sodium citrate) to wash the filter under the condition of 65° C. The hybridization can be performed in accordance with a method described in, for example, Molecular Cloning 2nd Ed.

Examples of DNAs that can hybridize under stringent conditions can include a DNA having a predetermined or higher level of homology to the nucleotide sequence of DNA used as a probe. It can be exemplified preferably by a DNA having, for example, 70% or higher, preferably 80% or higher, more preferably 90% or higher, even more preferably 95% or higher, particularly preferably 98% or higher, most preferably 99% or higher homology.

A method for obtaining or preparing a DNA of the present invention is not particularly limited. Appropriate probes or primers are prepared on the basis of information about the amino acid sequence or nucleotide sequence represented by SEQ ID NO: 1 or 2 disclosed herein, and they can be used to isolate the gene DNA of interest by screening a cDNA library predicted to contain the DNA. Alternatively, a DNA of the present invention can be prepared by chemical synthesis according to a standard method.

Specifically, by preparing a cDNA library according to a standard method from *Salicornia europaea* from which the gene DNA of the present invention has been isolated; subsequently selecting a desired clone from this library by use of appropriate probes specific to the gene DNA of the present invention, a gene DNA of the present invention can be obtained. The origin of the above-mentioned cDNA can be exemplified by a variety of cells or tissues derived from the aforementioned plant. All procedures such as separation of total RNA from these cells or tissues, separation and purification of mRNA, and acquisition and cloning of cDNA can be practiced according to a standard method. Examples of a method for screening the gene of the present invention from a cDNA library can include methods commonly used by those skilled in the art, such as a method described in Molecular Cloning 2nd Ed.

The mutant gene or homologous gene DNA of the present invention consisting of the nucleotide sequence represented by any one of (B) to (F) can be isolated by using the nucleotide sequence represented by SEQ ID NO: 1 or a DNA fragment having a portion thereof to screen a homolog of the DNA from other organisms and so on under appropriate conditions or can also be prepared by the above method for preparing the mutant DNA.

A method for obtaining/preparing a protein of the present invention is not particularly limited. The protein of the present invention may be any of an isolated naturally occurring protein, a chemically synthesized protein, and a recombinant protein prepared by a gene recombination technique. When the isolated naturally occurring protein is obtained, a protein of the present invention can be obtained from a cell or tissue with the expression of the naturally occurring protein by an appropriate combination of protein isolation and purification methods. When the protein is prepared by chemical synthesis, a protein of the present invention can be synthesized according to a chemical synthesis method such as an Fmoc method (fluorenylmethyloxycarbonyl method) or tBoc method (t-butyloxycarbonyl method). Alternatively, a protein of the present invention can also be synthesized with a variety of commercially available peptide synthesizers. When a protein is prepared by a gene recombination technique, a protein of the present invention can be obtained by introducing a DNA consisting of the nucleotide sequence encoding the protein into a suitable expression system. Among them, the preparation by a gene recombination technique, which can prepare the protein in large amounts by relatively easy procedures, is preferable.

For example, when a protein of the present invention is prepared by a gene recombination technique, a method known in the art including ammonium sulfate or ethanol precipitation, acid extraction, anion- or cation-exchange chromatography, phosphocellulose chromatography, hydrophobic interaction chromatography, affinity chromatography, hydroxyapatite chromatography, and lectin chromatography, preferably high-performance liquid chromatography, is used for recovering and purifying the protein from cell cultures. In particular, a purified product of the protein can be obtained by using for example, a column bound with an antibody such as a monoclonal antibody against a protein of the present invention, or when a usual peptide tag is added to the above protein of the present invention a column bound with a substance having affinity to the peptide tag, as a column used in affinity chromatography. When the protein of the present invention is expressed in a cell membrane, a purified sample can be obtained by allowing a cell membrane-degrading enzyme to act on the cell membrane and then performing the above-mentioned purification treatment.

Furthermore, the protein consisting of an amino acid sequence wherein one or a few amino acids are deleted, substituted, or added in the amino acid sequence represented by SEQ ID NO: 2 or the protein consisting of an amino acid sequence having 70% or higher homology to the amino acid sequence represented by SEQ ID NO: 2 can be prepared or obtained appropriately by those skilled in the art on the basis of information about the nucleotide sequence represented by SEQ ID NO: 1 showing one example of a nucleotide sequence encoding the amino acid sequence represented by SEQ ID NO: 2. For example, DNA having the nucleotide sequence represented by SEQ ID NO: 1 or a portion thereof can be used as a probe to screen and isolate a homolog of the DNA from an organism other than *Salicornia europaea* under appropriate conditions. The full-length DNA of this homolog DNA can be cloned, then incorporated into an expression vector, and expressed in an appropriate host to thereby produce a protein encoded by the homolog DNA.

The protein of the present invention can also be bound with a marker protein and/or a peptide tag and made into a fusion protein. The marker protein is not particularly limited as long as it is a conventionally known marker protein. Specific examples thereof can include enzymes such as alkaline phosphatase and HRP, antibody Fc domains, and fluorescent substances such as GFP. The peptide tag can be exemplified specifically by conventionally known peptide tags such as epitope tags (e.g., HA, FLAG, and Myc) and affinity tags (e.g., GST, maltose-binding proteins, biotinylated peptides, and oligohistidine). The fusion protein can be prepared according to a standard method and is useful in the purification of the protein of the present invention through the use of the affinity between Ni-NTA and a His tag, in the detection of the protein of the present invention, in the quantification of an antibody against the protein of the present invention, and as a reagent for research in the art.

The use of the DNA or protein of the present invention can improve the environmental stress tolerance such as salt tolerance, water stress tolerance (sorbitol tolerance), and heat tolerance of plants or animals, their tissues, organs, and cells, and microorganisms such as bacteria, yeast, and molds.

An antibody specifically binding to the protein of the present invention may be any antibody that specifically binds to the above-mentioned protein of the present invention. Specific examples of the antibody can include immunospecific antibodies such as monoclonal antibodies, polyclonal antibodies, chimeric antibodies, single chain antibodies, and humanized antibodies. These antibodies can be prepared by using as an antigen, the protein consisting of the amino acid sequence represented by SEQ ID NO: 2, the protein consisting of an amino acid sequence having 70% or higher homology to the amino acid sequence represented by SEQ ID NO: 2 and having an activity of improving a tolerance to at least heat or water stress, or the protein consisting of an amino acid sequence wherein one or a few amino acids are deleted, substituted, or added in the amino acid sequence represented by SEQ ID NO: 2 and having an activity of improving a tolerance to at least heat or water stress. These antibodies are useful, for example, in elucidating the molecular mechanism of a protein having an activity of improving a tolerance to an environmental stress.

The antibody against the above-mentioned protein having an activity of improving a tolerance to at least heat or water stress is produced according to a routine protocol by administering to animals (preferably, other than humans), the protein having an activity of improving a tolerance to at least heat or water stress or a fragment, analog, or cell containing the epitope thereof. For example, in the preparation of monoclonal antibodies, any technique such as a hybridoma technique (Nature 256, 495-497, 1975), a trioma technique, a human B cell hybridoma technique (Immunology Today 4, 72, 1983), and an EBV-hybridoma technique (MONOCLONAL ANTIBODIES AND CANCER THERAPY, pp. 77-96, Alan R. Liss, Inc., 1985), which provide antibodies produced from cultures of a continuous cell line, can be used.

A method for preparing a single chain antibody (U.S. Pat. No. 4,946,778) can be applied to the preparation of single chain antibodies against the above-mentioned protein having an activity of improving a tolerance to at least heat or water stress. To express humanized antibodies, for example, a transgenic plant or transgenic animal can be utilized. Alternatively, the above-mentioned antibody can be used to isolate/identify a clone expressing the protein having an activity of improving a tolerance to an environmental stress or to purify a polypeptide thereof by affinity chromatography.

The recombinant vector of the present invention is not particularly limited as long as it is a recombinant vector comprising the DNA of the present invention and that can express the protein having an activity of improving a tolerance to at least heat or water stress. The recombinant vector of the present invention can be constructed by appropriately integrating the gene DNA of the present invention into an expression vector. The expression vector is preferably those capable of autonomously replicating in a host cell or those capable of being incorporated into a chromosome of a host cell. Alternatively, those containing regulatory sequences such as a promoter, an enhancer, and a terminator at positions where a gene of the present invention can be expressed can be used preferably.

For example, an expression vector for a plant cell can be exemplified by plasmids such as Ti plasmids (Tumor inducing plasmids), pSPORT1, pT7Blue-T vectors, pIG121-Hm [Plant Cell Report, 15, 809-814 (1995)], and pBI121 [EMBO J. 6, 3901-3907 (1987)] or plant virus vectors such as tobacco mosaic virus, cauliflower mosaic virus, and Geminivirus. Examples of a promoter for a plant cell can include cauliflower mosaic virus 35S promoters [Mol. Gen. Genet (1990) 220, 389-392] and ribulose bisphosphate carboxylase small subunit promoters. Examples of a terminator can include a terminator of a nopaline synthase gene.

An expression vector for yeast can be exemplified by pYES2 (Invitrogen), YEp13 (ATCC37115), YEp24 (ATCC37051), Ycp5O (ATCC37419), pHS19, and pHS15. Specific examples of a promoter for yeast can include promoters such as PHO5 promoters, PGK promoters, GAP promoters, ADH promoters, gal1 promoters, gal10 promoters, heat shock protein promoters, MFα1 promoters, and CUP1 promoters. An expression vector for yeast, a plant cell, a bacterium, an animal cell, or the like, can be used as the expression vector. A recombinant vector using the expression vector for yeast or a plant cell is preferable.

An expression vector for a bacterium can be exemplified by pBTrP2, pBTac1, and pBTac2 (all manufactured by Boehringer Mannheim), pKK233-2 (manufactured by Pharmacia), pSE280 (manufactured by Invitrogen), pGEMEX-1 (manufactured by Promega), pQE-8 (manufactured by QIAGEN), pQE-30 (manufactured by QIAGEN), pKYP10 (Japanese Laid-Open Patent Application No. 58-110600), pKYP200 [Agric. Biol. Chem., 48, 669(1984)], pLSA1 [Agric. Biol. Chem., 53, 277 (1989)], pGEL1 [Proc. Natl. Acad. Sci. USA, 82, 4306 (1985)], pTP5, pC194, pUC18 [Gene, 33, 103 (1985)], pUC19 [Gene, 33, 103 (1985)], pSTV28 (manufactured by Takara Shuzo Co., Ltd.), and pSTV29 (manufactured by Takara Shuzo Co., Ltd.). Examples of a promoter for a bacterium can include: promoters derived from *Escherichia coli*, a phage, and so on, such as trp promoters (Ptrp), lac promoters (Plac), PL promoters, PR promoters, and PSE promoters; and SP01 promoters, SP02 promoters, and penP promoters.

The transformed cell of the present invention is not particularly limited as long as it is a transformed cell comprising the above-mentioned recombinant vector of the present invention introduced therein and expressing the protein having an activity of improving a tolerance to at least heat or water stress. The transformed cell can include transformed plant cells, transformed animal cells, transformed bacteria, and transformed yeast and can be exemplified preferably by transformed *Escherichia coli*, transformed yeast, and transformed plant cells. These transformed cells such as transformed *Escherichia coli*, transformed yeast, and transformed plant cells can be applied preferably to various microorganism industries such as amino acid production.

A host plant cell used for preparing transformed plant cells is not particularly limited by its type and can be selected appropriately from cultured cells of plants such as ornamental flowers, fruit plants, vegetables, root vegetables, cereals, foliage plants, and trees including fruit-trees, for example, plants belonging to the family Solanaceae, Poaceae, Brassicaceae, Asteraceae, Pedaliaceae, Oleaceae, Myrtaceae, Rosaceae, Leguminosae, Arecaceae, or Rubiaceae. To prepare this transformed plant cell, a method wherein the recombinant vector of the present invention comprising the gene DNA of the present invention is used and introduced into a plant cell to thereby introduce the gene DNA of the present invention into the genomic DNA in the plant cell, can be adopted. The plant transformation can be performed by appropriately using a method known in the art such as a leaf-disk cocultivation method, electroporation, *Agrobacterium* method, or particle gun method according to a plant type and so on. In addition, a method wherein a transformed plant is prepared by physically or chemically enhancing the permeability of a plant cell and directly incorporating the recombinant vector of the present invention into the receptor cell, can also be adopted.

Specific examples of a yeast host used for preparing transformed yeast can include *Saccharomyces cerevisiae, Schizosaccharomyces pombe, Kluyveromyces lactis, Trichosporon pullulans*, and *Schwanniomyces alluvius*. Examples of a method for introducing a recombinant vector into a yeast host can include electroporation, a spheroplast method, and a lithium acetate method.

Specific examples of a host bacterial cell used for preparing transformed bacteria can include microorganisms belonging to the genera *Escherichia, Corynebacterium, Brevibacterium, Bacillus, Microbacterium, Serratia, Pseudomonas, Agrobacterium, Arthrobacter, Erwinia, Methylobacterium, Rhodobacter, Streptomyces,* and *Zymomonas*. Examples of a method for introducing a recombinant vector into a bacterium host can include a method using calcium ions and a protoplast method.

A method for producing the protein having an activity of improving a tolerance to at least heat or water stress of the present invention is not particularly limited as long as it is a method comprising culturing the above-mentioned transformed cell of the present invention such as transformed yeast, transformed bacteria, and transformed plant cells and recovering a recombinant protein from the transformed cell or a supernatant of the culture solution thereof. Furthermore, a transgenic plant of the present invention is not particularly limited as long as it is obtained by introducing the DNA encoding the protein having an activity of improving a tolerance to at least heat or water stress or the above-mentioned vector into a plant cell and allowing the plant cell to divide, proliferate, and redifferentiate. Hereinafter, the above-mentioned vector, the transformed cell, the method for producing a protein having an activity of improving a tolerance to an environmental stress, and the transgenic plant of the present invention will be described.

As described above, the DNA of the present invention can be utilized in the preparation of a recombinant protein. The preparation of a recombinant protein can be performed by inserting the above-mentioned DNA of the present invention into an appropriate expression vector, introducing the vector into an appropriate host cell, allowing the host cell to express the DNA, and then recovering the expressed protein from the transformed cell or a culture supernatant thereof. Examples of a host-vector system used in recombinant protein expression can include IMPACT-CN System (host: *E. coli* strain ER2566, vector: pTYB1, pYB2, pYB11, and pYB12 (BioLabs)) and pET Expression System (host: *Epicurian Coli* BL21, vector: pET3 series (Novagen)). Examples of a method for introducing a vector into a host cell include methods generally known by those skilled in the art, for example, electroporation and a heat shock method (Method for Preparing Gene Library, Yodosha Co., Ltd. (1994); and Introductory Manual on Plant Cell Technology, Japan Scientific Societies Press (1998)). The transformant for expressing the recombinant protein can be cultured by a method and conditions generally used by those skilled in the art. The expressed protein can be purified by, for example, chitin beads (BioLabs) for the IMPACT-CN System used or His Bind Resin (Novagen) for the pET Expression System used.

The DNA of the present invention can also be utilized in the production of a transgenic plant having an enhanced tolerance to at least heat or water stress. An organism species for producing a transgenic plant by use of the DNA of the present invention is not particularly limited and is preferably a higher plant. The production of a transgenic plant can be performed advantageously by inserting the DNA into a vector that secures its expression in a plant cell, introducing this vector into a plant cell, and regenerating the transformed plant cell for obtaining a transgenic plant.

For example, pBI101 commercially available from TOYOBO Co., Ltd. or pIG121Hm (Plant J, Vol 6, p 271-282 (1994)) can be used preferably as a vector used in the production of a transgenic plant. The type of a plant cell into which the vector is introduced is not particularly limited, and a possible plant cell is, for example, rice, wheat, corn, soybean, tobacco, or carrot. The form of the plant cell is, for example, a protoplast, a callus, or a portion of a plant (e.g., leaf disk or hypocotyl). As a method for introducing a vector into a host plant cell, an *Agrobacterium* method is preferred. In addition, for example, a polyethylene glycol method, electroporation, and a particle gun method can also be used (Experimental Protocol for Model Plants, Shujunsha Co., Ltd., 1996).

A method for regenerating a plant cell comprising a vector introduced therein into a plant differs depending on a plant species. For example, for rice, the method can be carried out as follows: a callus is induced from a mature seed and infected with *Agrobacterium* comprising cDNA introduced therein. After cocultivation, the callus is transferred to a selective medium and cultured. After approximately 3 weeks, the callus is transferred to a redifferentiation medium and cultured until it redifferentiates. After acclimation for 4 or 5 days, the transformant is transferred to a pot and regenerated (Experimental Protocol for Model Plants, Shujunsha Co., Ltd., 1996). Regeneration methods for, for example, carrot and tobacco can be exemplified preferably by the methods of Prof. Kato and Prof. Shono, respectively (Techniques of Plant Tissue Culture, Asakura Publishing Co., Ltd., 1983).

If a transgenic plant is obtained by this procedure, reproduction materials (culture and proliferation of e.g., seeds, tuberous roots, cuttings, or mericlones, according to a plant type) are further obtained from the plant. The transgenic plant of the present invention can be mass-produced on the basis of the reproduction materials.

Hereinafter, the present invention will be described more specifically with reference to Examples. However, the technical scope of the present invention is not intended to be limited to these illustrations.

Example 1

Preparation of *Salicornia europaea* cDNA Library

*Salicornia europaea* is an annual herb belonging to the family Chenopodiaceae of the class Dicotyledoneae of the phylum Angiospermae and shows the highest level of salt tolerance (which can grow even at 1 M or higher NaCl concentrations) among higher plants. A *Salicornia europaea* cDNA library was prepared with the leaves according to procedures shown below. First, total mRNA was extracted according to the method of Ostrem et al. (Plant Physiol Vol. 84 p 1270-1275 (1987)). Poly(A)+RNA was purified from this total mRNA by use of Oligotex-dT30 <super> (Daiichi Pure Chemicals Co., Ltd). cDNA was synthesized on the basis of the purified poly(A)+RNA and introduced into a λZap II (Stratagene) lambda phage vector to construct a cDNA library. A method for constructing a cDNA library by use of λZap II is a well known method, and the actual procedure was performed according to the manual of Stratagene. As a result, the *Salicornia europaea* cDNA library containing $5 \times 10^5$ independent clones was successfully constructed.

Example 2

Figure 1:
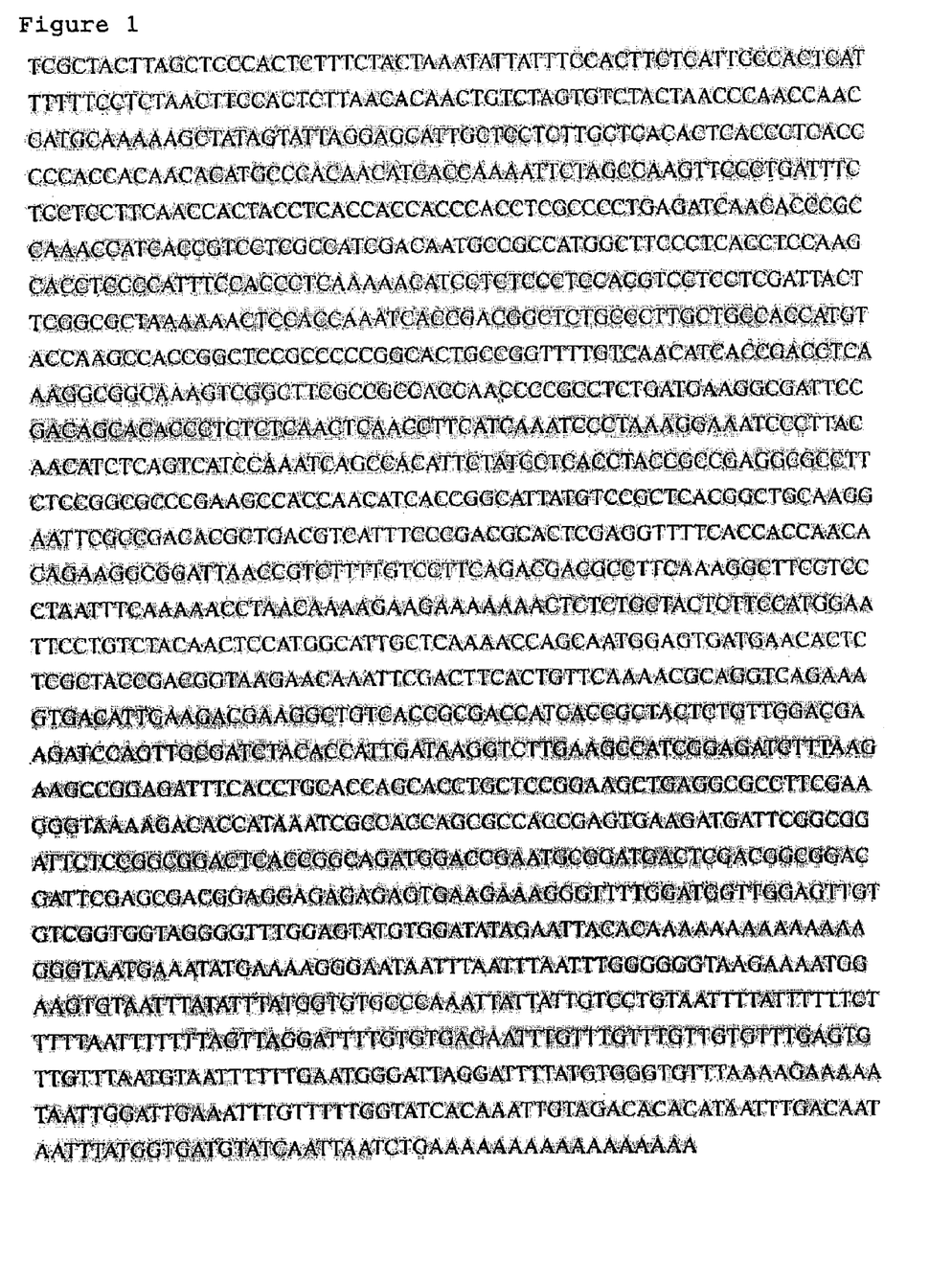
FIG. 1 shows the nucleotide sequence of cDNA encoding SeFLA having an ability to enhance environmental stress tolerance.
Figure 2:
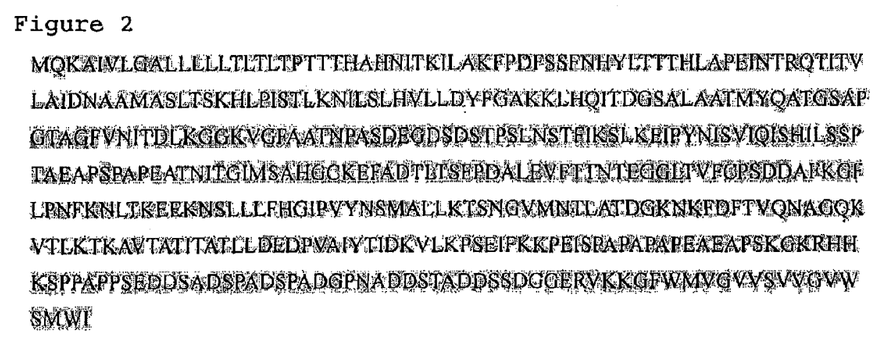
FIG. 2 shows the amino acid sequence of SeFLA having an ability to enhance environmental stress tolerance.

Search for Environmental Stress Tolerance Gene from *Salicornia europaea* cDNA Library Environmental stress tolerance genes were searched from the *Salicornia europaea* cDNA library according to a functional screening method using *Escherichia coli*, which was developed by Yamada et al. (Plant Cell Physiol Vol. 43 p 903-910 (2002)). As a result, improvement in salt tolerance was observed in *Escherichia coli* in which cDNA of 1765 by in full length shown in FIG. 1 was introduced. As a result of nucleotide sequence analysis with genetic information processing software (Software Development Co., Ltd.), the nucleotide sequence has been shown to encode a protein consisting of 427 amino acids. The BLAST homology search program was used to perform homology search for the amino acid sequence encoded by the DNA. As a result, the amino acid sequence shown in FIG. 2 was confirmed to have partial homology (58% homology was found in a region at the positions 1 to 427 of the amino acid sequence of FIG. 2) to a Fasciclin-like arabinogalactan protein (FLA1) (At5g55730) of *Arabidopsis thaliana*. As a result of analysis using SignalP, the amino acid sequence at the positions 1 to 25 of this protein (hereinafter, SeFLA) was considered to be a secretory signal peptide. Moreover, as a result of analyses using DGPI and big-PI plant predictor, the C-terminal amino acid sequence at the positions of 412 to 427 of SeFLA and the amino acid sequence at the positions of 401 and 402 were considered to be a hydrophobic glycosylphosphatidylinositol (GPI) anchor signal sequence, respectively, from the former and the latter analyses.

Example 3

Preparation of Partial-Length SeFLA cDNA

Figure 3:
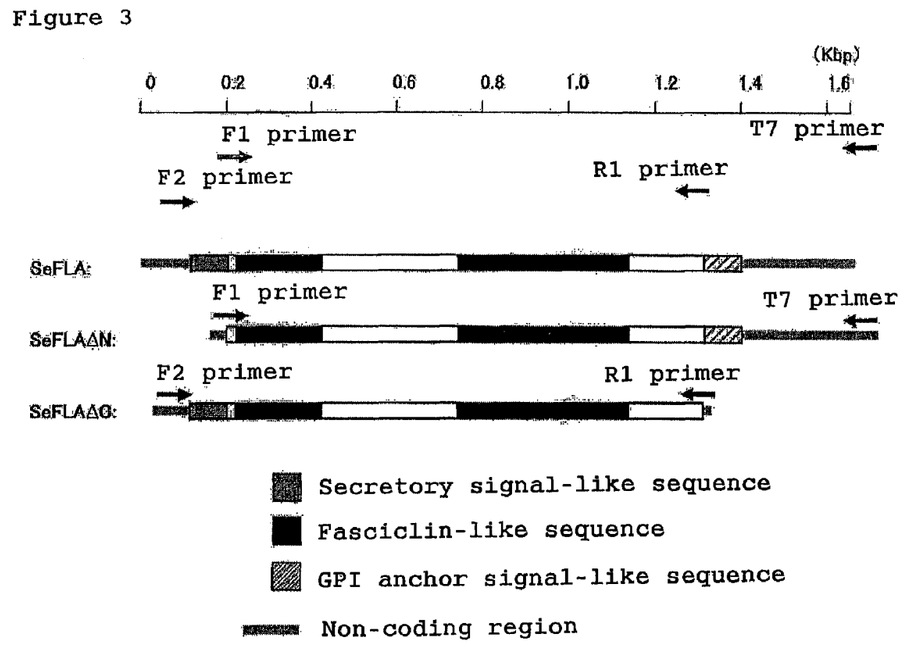
FIG. 3 is a schematic diagram of SeFLA having an ability to enhance environmental stress tolerance and cDNA encoding the SeFLA. Primers used for preparing subclones (SeFLAΔN and SeFLAΔC) comprising an initiation codon artificially added thereto by PCR are shown.

A partial-length sequence (SeFLAΔN) of SeFLA from which the amino acid sequence of the putative secretory signal peptide at the positions 1 to 25 was removed was amplified by PCR using an F1 primer (5'-CCCACCACAACATAAATGCACAACATCACC-3'; SEQ ID NO: 3) and a T7 primer (5'-GTAATACGACTCACTATAGGGC-3'; SEQ ID NO: 4) and using as a template, the full-length SeFLA cDNA (cloned into pBluescript SK) obtained by the above-mentioned screening (FIG. 3). The obtained DNA fragment was blunted with T4 DNA Polymerase and klenow. On the other hand, pBluescript SK, an *Escherichia coli* expression vector, was cleaved with EcoRV and treated with alkaline phosphatase. Then, the above-mentioned PCR fragment was cloned into the resulting vector. The cloned fragment was confirmed to have no mutation and used in subsequent experiments. Moreover, a partial-length sequence (SeFLAΔC) of SeFLA from which the amino acid sequence of the putative GPI anchor signal sequence at the positions 401 to 427 was removed was amplified in the same way as above by PCR using an F2 primer (5'-GTCTAGTGTCTACTAACCCAACCAACCATG-3'; SEQ ID NO: 5) and an R1 primer (5'-CTCTCCTCCGTCTCACTAATCGTCCGCCGT-3'; SEQ ID NO: 6) (FIG. 3). The obtained DNA fragment was blunted with T4 DNA Polymerase and klenow. On the other hand, pBluescript SK, an *Escherichia coli* expression vector, was cleaved with EcoRV and treated with alkaline phosphatase. Then, the above-mentioned PCR fragment was cloned into the resulting vector. The cloned fragment was confirmed to have no mutation and used in subsequent experiments.

Initiation codons on the primers are indicated by double-width characters, and termination codons thereon are underlined.

Example 4

Cloning into Yeast Expression Vector

The full-length SeFLA cDNA or each partial-length SeFLA (SeFLAΔN or SeFLAΔC) cDNA cloned into pBluescript SK was cleaved with KpnI, then blunted with T4 DNA Polymerase and klenow, and cleaved with SacI. The obtained fragments were cloned into the SacI/HpaI sites of yeast expression vectors (pAUR123; Takara Shuzo Co., Ltd.) having an ADH1 promoter. The obtained plasmids were cleaved with SmaI and self-ligated to thereby remove redundant restriction enzyme sites occurring in non-coding regions during cloning.

Example 5

Cloning into Plant Expression Vector

The full-length SeFLA cDNA cloned into pBluescript SK was cleaved with KpnI, then blunted with T4 DNA Polymerase and klenow, and cleaved with XbaI. The obtained fragment was cloned into plant expression vectors (pBI121) having a 35S cauliflower mosaic virus promoter so that the fragment was located downstream of the promoter.

Example 6

Preparation of Transformed *Agrobacterium tumefaciens*

To prepare tobacco transformants comprising the SeFLA (full length) cDNA introduced therein, the above-mentioned plasmids were introduced into *A. tumefaciens* (EHA strains) by electroporation (GTE-10; Shimadzu Corp). The transformants obtained by selection in a YEP solid medium containing 50 μg/ml hygromycin were inoculated into a YEP medium containing hygromycin and shake-cultured at 28° C.

Example 7

Gene Transfer to Tobacco by *Agrobacterium* Method

The transformed *A. tumefaciens* comprising the SeFLA (full length) cDNA introduced therein was diluted to $OD_{600}$=0.25 with an acetosyringone solution (10 μg/ml). A leaf disk (7 mm in diameter) of a tobacco leaf grown under aseptic conditions was produced and dipped into this bacterial cell suspension for 1 minute. This leaf disk was placed in a Murashige-Skoog (MS) solid medium containing 10 μg/ml acetosyringone and incubated at 26° C. for 2 days under dark conditions. Then, the leaf disk was placed in an MS redifferentiation medium (which contained benzylaminopurine: 0.05 mg/ml, naphthylacetic acid: 0.05 mg/ml, Claforan: 250 mg/ml, and kanamycin: 100 mg/ml) and cultured at 26° C. under light/dark conditions. The leaf disk was transferred to a fresh medium every two weeks. After approximately 1 month, shoots redifferentiated from the leaf disk were cut out and planted in an MS rooting medium (which contained Claforan: 250 mg/ml and kanamycin: 100 mg/ml). Each transformed tobacco grown for approximately 2 months was transferred to soil to obtain next-generation (T1) seeds after approximately 4 months.

Example 8

Salt Stress Tolerance-Enhancing Function of SeFLA for *Escherichia coli*

Figures 4, 4A:
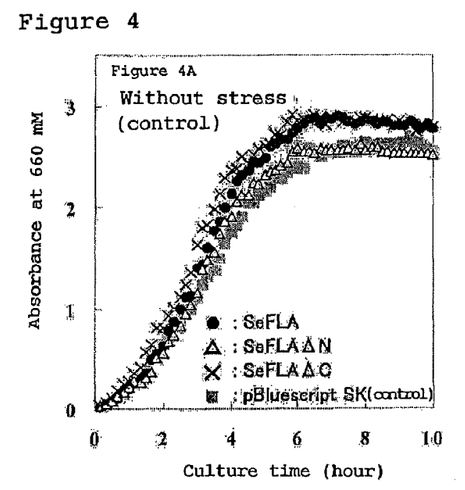
FIG. 4 shows the salt, moisture (sorbitol), and heat stress tolerance of transformed Escherichia coli in which cDNA encoding SeFLA having an ability to enhance environmental stress tolerance or partial-length cDNA thereof (an initiation codon artificially added thereto by PCR) has been introduced.
Figure 4B:
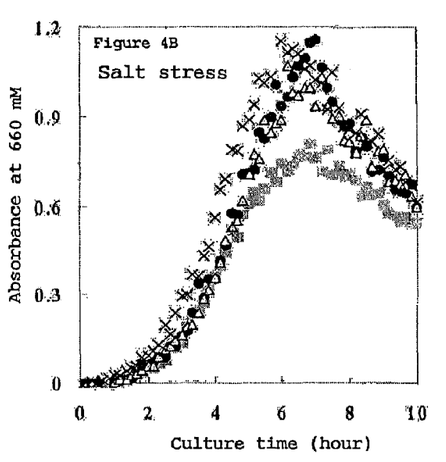

Transformants obtained by introducing the full-length SeFLA cDNA or each partial-length SeFLA (SeFLAΔN or SeFLAΔC) cDNA cloned into pBluescript SK into *Escherichia coli* (SOLR; Stratagene) were evaluated for their growth. Each transformant was inoculated at an initial concentration of $OD_{600}$=0.05 into a 2YT liquid medium, and the bacterial cell concentration was monitored with a compact rocking incubator TVS062CA (ADVANTEC). All the transformants showed almost equal growth under conditions without stress (NaCl: 86 mM, sorbitol: 0 mM, 37° C.) (FIG. 4A), whereas evident improvement in salt tolerance was observed at 37° C. in a 2YT liquid medium (sorbitol: 0 mM) containing 650 mM NaCl in the transformant comprising the full-length SeFLA or partial-length SeFLA (SeFLAΔN or SeFLAΔC) introduced therein, as compared with a transformant comprising a vector (pBluescript SK) introduced therein as a control (FIG. 4B).

Example 9

Water Stress Tolerance-Enhancing Function of SeFLA for *Escherichia coli*

Figure 4C:
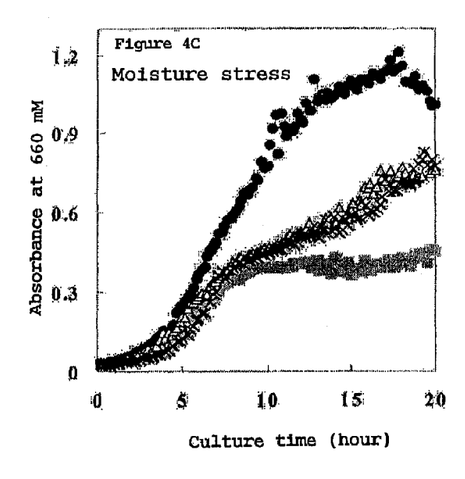

Transformants comprising the full-length SeFLA cDNA or each partial-length SeFLA (SeFLAΔN or SeFLAΔC) cDNA or a vector (pBluescript SK) as a control introduced therein were evaluated for their water stress tolerance. The same procedure as in Example 8 was performed at 37° C. with a 2YT medium (NaCl: 86 mM) containing 1.2 M sorbitol. As a result, remarkable proliferation was observed in the transformant comprising the full-length SeFLA introduced therein, as compared with the transformant comprising only the vector as a control introduced therein. This demonstrated that SeFLA has a function of enhancing water stress tolerance for *Escherichia coli*. The transformant comprising the partial-length SeFLA (SeFLAΔN or SeFLAΔC) introduced therein was shown to have a reduced proliferation rate under the same conditions, as compared with the transformant comprising the full-length SeFLA introduced therein (FIG. 4C).

Example 10

Heat Stress Tolerance-Enhancing Function of SeFLA for *Escherichia coli*

Figure 4D:
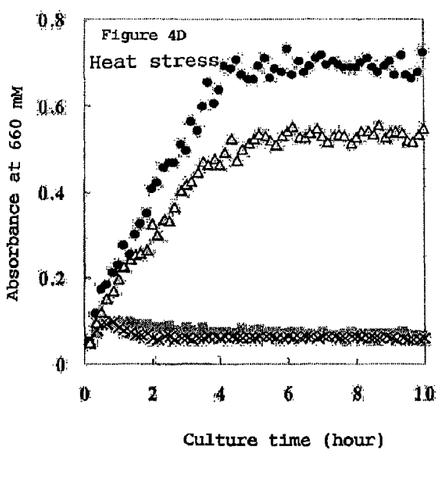

Transformants comprising the full-length SeFLA cDNA or each partial-length SeFLA (SeFLAΔN or SeFLAΔC) cDNA or a vector (pBluescript SK) as a control introduced therein were evaluated for their heat stress tolerance. The same procedure as in Example 8 was performed to draw a proliferation curve under the condition of 45° C. with a usual 2YT liquid medium (NaCl: 86 mM, sorbitol: 0 mM). As a result, remarkable proliferation was observed in the transformant comprising the full-length SeFLA introduced therein. The transformed *Escherichia coli* comprising the SeFLAΔN introduced therein was confirmed to have a reduced proliferation rate as compared with the transformant comprising the full-length SeFLA introduced therein but remarkably proliferate as compared with the control. The SeFLAΔC was at the same level as the control (FIG. 4D). These results demonstrated that SeFLA functions as a factor enhancing salt, moisture, and heat stress tolerance for *Escherichia coli*. The sufficient function of this protein required both the region of the putative secretory signal peptide and the region of the putative GPI anchor signal sequence.

Example 11

Salt Stress Tolerance-Enhancing Function of SeFLA for Yeast

Figures 5, 5A:
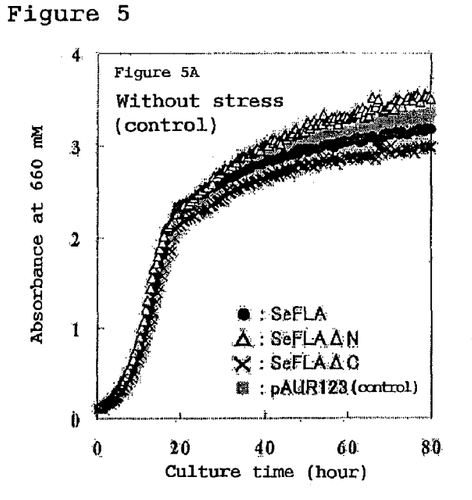
FIG. 5 shows the salt, moisture (sorbitol), and heat stress tolerance of transformed yeast in which cDNA encoding SeFLA having an ability to enhance environmental stress tolerance or partial-length cDNA thereof has been introduced.
Figure 5B:
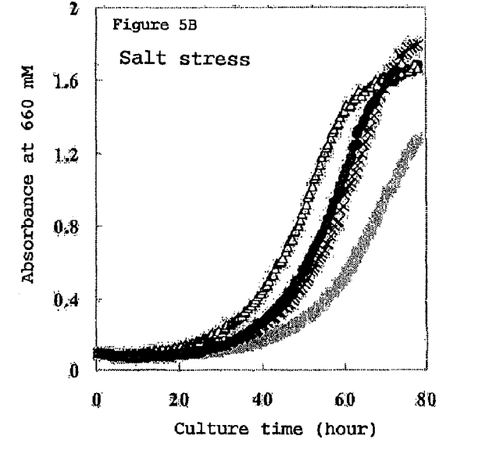

Transformants obtained by introducing the full-length SeFLA or each partial-length SeFLA (SeFLAΔN or SeFLAΔC) cloned into pAUR123 (yeast expression vector) into *Saccharomyces cerevisiae* (YM4271; Clontech) were evaluated for their salt tolerance. Each transformant was transferred at an initial concentration of $OD_{600}$=0.1 to a YPD liquid medium, and change in cell concentration was monitored with a compact rocking incubator TVS062CA (ADVANTEC). All the transformed yeasts showed almost equal growth under conditions without stress (NaCl: 0 mM, sorbitol: 0 mM, 30° C.) (FIG. 5A). By contrast, evident improvement in salt tolerance was observed in a YPD liquid medium containing 1.5 M NaCl in the transformant comprising the full-length SeFLA or each partial-length SeFLA (SeFLAΔN or SeFLAΔC) introduced therein, as compared with a transformant comprising only the vector introduced therein (FIG. 5B).

Example 12

Water Stress Tolerance-Enhancing Function of SeFLA for Yeast

Figure 5C:
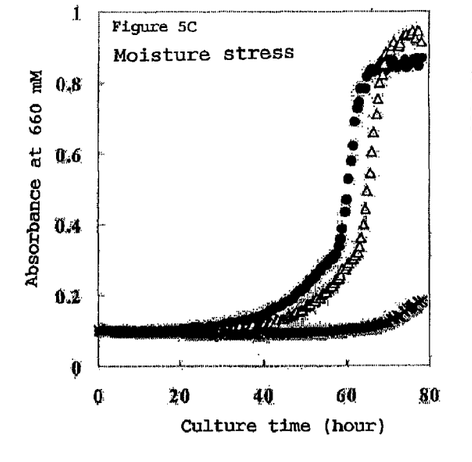

Transformants comprising the full-length SeFLA or each partial-length SeFLA (SeFLAΔN or SeFLAΔC) or a vector (pAUR123) as a control introduced therein were evaluated for their water stress tolerance. The same procedure as in Example 11 was performed under the condition of 30° C. with a YPD medium (NaCl: 0 mM) containing 2.2 M sorbitol. As a result, remarkable proliferation was observed in the transformant comprising the full-length SeFLA or SeFLAΔC introduced therein, as compared with the control (FIG. 5C). No remarkable difference was observed between the transformant comprising the SeFLAΔC introduced therein and the control under the same conditions (FIG. 5C). These results demonstrated that SeFLA functions as a factor enhancing water stress tolerance in yeast, and the region of the putative GPI anchor signal sequence is particularly essential.

Example 13

Heat Stress Tolerance-Enhancing Function of SeFLA for Yeast

Figure 5D:
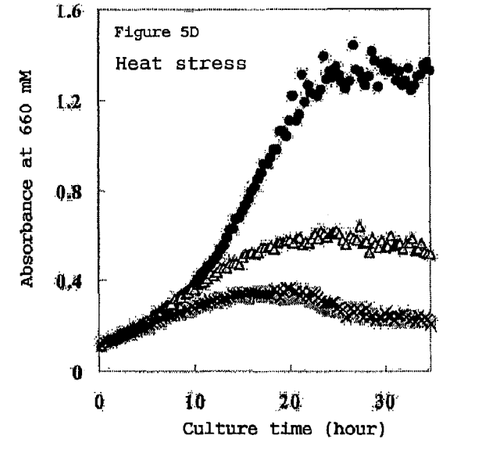

Transformants comprising the full-length SeFLA or partial-length SeFLA (SeFLAΔN or SeFLAΔC) or a vector (pAUR123) as a control introduced therein were evaluated for their heat stress tolerance. The same procedure as in Example 11 was performed to evaluate growth at 38° C. with a YPD liquid medium (NaCl: 0 mM, sorbitol: 0 mM). As a result, remarkable proliferation was observed in the transformant comprising the full-length SeFLA introduced therein, as compared with the control. The transformant comprising the SeFLAΔN introduced therein was confirmed to have a reduced proliferation rate as compared with the transformant comprising the full-length SeFLA introduced therein but remarkably proliferate as compared with the control. The transformant comprising the SeFLAΔC introduced therein had a proliferation rate extremely reduced to a level equal to that of the control (FIG. 5D). These results demonstrated that SeFLA also functions as a factor enhancing heat tolerance in yeast, and the region of the putative GPI anchor signal sequence is particularly essential.

These results demonstrated that SeFLA functions as a factor enhancing salt, moisture, and heat stress tolerance for yeast.

Example 14

Salt Stress Tolerance-Enhancing Function of SeFLA for Tobacco

Figure 6A:
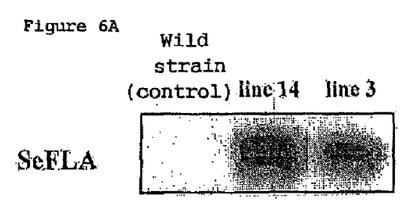
FIG. 6 shows the salt and moisture (mannitol) stress tolerance of transformed tobacco in which cDNA encoding SeFLA having an ability to enhance environmental stress tolerance has been introduced.
Figure 6B:
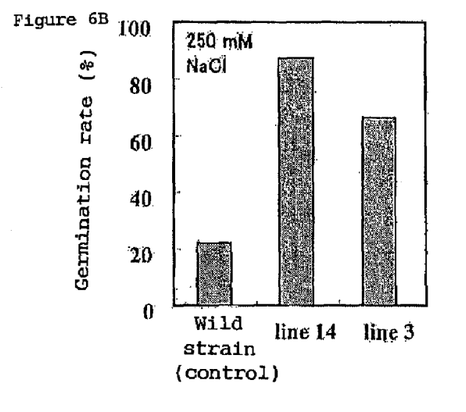
Figure 6C:
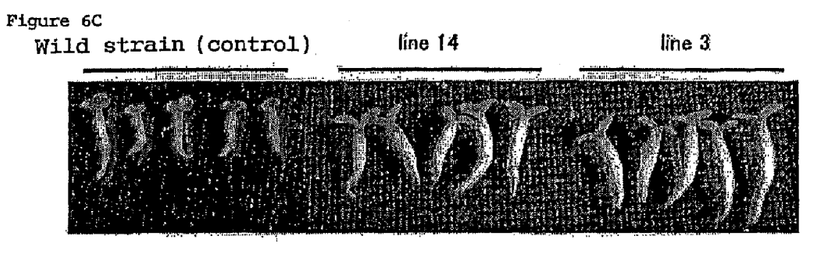
Figure 6D:
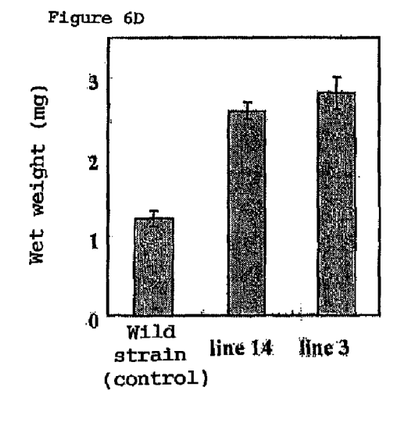

A total of 14 lines of transformed tobaccos prepared according to Example 7 were produced, and SeFLA mRNA expression in each transformant was confirmed by northern blotting. As a result of using the full-length SeFLA cDNA as a probe, SeFLA mRNA was confirmed to be strongly expressed in the lines 3 and 14 (FIG. 6A). Thus, these two lines were self-pollinated to obtain next-generation (T1) seeds. The obtained seeds were inoculated into soil and then fed every 4 days with salt water containing 250 mM NaCl. After 10 days, germination rate was evaluated. As a result, remarkable improvement in germination rate in the presence of NaCl was observed in the transformant comprising the full-length SeFLA introduced therein, as compared with a wild strain as a control (FIG. 6B). An evident difference in growth was observed between the seedling plant germinated from this transformant and that from the control (FIG. 6C). A remarkable difference in wet weight was also observed therebetween (FIG. 6D).

Figure 6E:
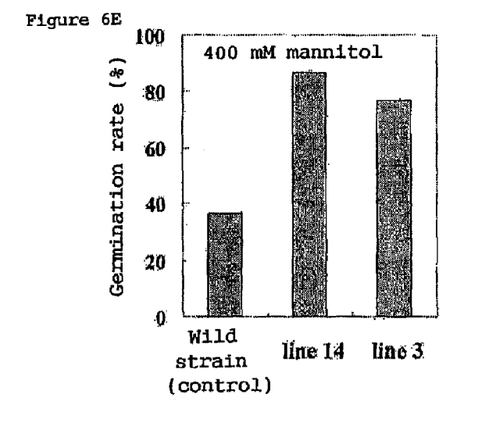

The above results demonstrated that SeFLA has an effect of improving the salt, moisture, and heat stress tolerance of a wide range of organism species from bacteria to yeast. Particularly, these stresses bring about reduction in intracellular moisture content for a variety of cells. Therefore, the SeFLA protein was considered to have an effect of preventing reduction in intracellular moisture content. In fact, the lines 14 and 3 of transformed tobaccos comprising the SeFLA introduced therein were respectively confirmed to have improvement in germination rate (evaluated for 10 days) in an agar medium containing 400 mM mannitol (FIG. 6E).

---

The invention claimed is:

1. An isolated DNA sequence comprising a polynucleotide encoding a protein having the amino acid sequence represented by SEQ ID NO: 2.

2. An isolated DNA sequence comprising a polynucleotide encoding a protein having 90% or higher amino acid sequence identity to the amino acid sequence represented by SEQ ID NO: 2 and having an activity of improving a tolerance to at least heat or water stress of a cell expressing said protein when compared to a cell not expressing said protein.

3. An isolated DNA sequence comprising a polynucleotide encoding a protein having an amino acid sequence wherein 1-30 amino acids are deleted, substituted, or added in the amino acid sequence represented by SEQ ID NO: 2 and having an activity of improving a tolerance to at least heat or water stress of a cell expressing said protein when compared to a cell not expressing said protein.

4. An isolated DNA sequence comprising the nucleotide sequence represented by SEQ ID NO:1 or the full-length complementary sequence thereof.

5. An isolated DNA sequence comprising a nucleotide sequence wherein 1-20 bases are deleted, substituted, or added in the nucleotide sequence represented by SEQ ID NO: 1 and encoding a protein having an activity of improving a tolerance to at least heat or water stress of a cell expressing said protein when compared to a cell not expressing said protein.

6. An isolated DNA sequence hybridizing under stringent conditions to the DNA having the full-length complementary sequence to SEQ ID NO: 1 and encoding a protein having an activity of improving a tolerance to at least heat or water stress of a cell expressing said protein when compared to a cell not expressing said protein, wherein said stringent conditions comprises a wash using 0.1-fold SSC solution under the condition of 65° C.

7. A recombinant vector comprising the DNA according to any one of claims 1 to 6.

8. A transformed cell obtained by introducing into a host cell a recombinant vector comprising the DNA according to any one of claims 1 to 6.

9. A transformed cell obtained by introducing into a plant cell a recombinant vector comprising the DNA according to any one of claims 1 to 6.

10. A transformed cell obtained by introducing into a microorganism cell a recombinant vector comprising the DNA according to any one of claims 1 to 6.

* * * * *